(12) United States Patent
Giovannini et al.

(10) Patent No.: US 12,398,143 B2
(45) Date of Patent: *Aug. 26, 2025

(54) IMIDAZOPYRAZINE DERIVATIVES AND THE USE THEREOF AS MEDICAMENT

(71) Applicant: Boehringer Ingelheim International GmbH, Ingelheim am Rhein (DE)

(72) Inventors: Riccardo Giovannini, Biberach an der Riss (DE); Dieter Wiedenmayer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 881 days.

This patent is subject to a terminal disclaimer.

(21) Appl. No.: 17/616,205

(22) PCT Filed: Jun. 3, 2020

(86) PCT No.: PCT/EP2020/065253
§ 371 (c)(1),
(2) Date: Dec. 3, 2021

(87) PCT Pub. No.: WO2020/245137
PCT Pub. Date: Dec. 10, 2020

(65) Prior Publication Data
US 2022/0306637 A1   Sep. 29, 2022

(30) Foreign Application Priority Data
Jun. 4, 2019 (EP) .................................. 19178045

(51) Int. Cl.
*C07D 487/04* (2006.01)
*A61K 47/00* (2006.01)
*A61P 43/00* (2006.01)
*C07D 241/38* (2006.01)
*C07D 519/00* (2006.01)

(52) U.S. Cl.
CPC ............ *C07D 487/04* (2013.01); *A61K 47/00* (2013.01); *A61P 43/00* (2018.01); *C07D 241/38* (2013.01); *C07D 519/00* (2013.01)

(58) Field of Classification Search
CPC .... A61K 47/00; C07D 241/38; C07D 487/04; C07D 519/00; A61P 43/00
See application file for complete search history.

(56) References Cited

U.S. PATENT DOCUMENTS

| 10,030,026 B2 | 7/2018 | Shapiro |
| 10,849,907 B2 | 12/2020 | Giovannini et al. |
| 2002/0055519 A1 | 5/2002 | Thompson et al. |

FOREIGN PATENT DOCUMENTS

| WO | 2002080928 A1 | 10/2002 |
| WO | 2003010159 A1 | 2/2003 |
| WO | 2004048364 A1 | 6/2004 |
| WO | 200610969 A1 | 2/2006 |
| WO | 2006113471 A2 | 10/2006 |
| WO | 2007067511 A2 | 6/2007 |
| WO | 2010088408 A2 | 8/2010 |
| WO | 2012128582 A2 | 9/2012 |
| WO | 2014060398 A1 | 4/2014 |
| WO | 2015080904 A1 | 6/2015 |
| WO | 2015130905 A1 | 9/2015 |
| WO | 2016006593 A1 | 1/2016 |
| WO | 2016029146 | 2/2016 |
| WO | 2016029146 A1 | 2/2016 |
| WO | 2016049165 A1 | 3/2016 |
| WO | 2016100349 A2 | 6/2016 |
| WO | 2017066368 A1 | 4/2017 |
| WO | 2019110703 A1 | 6/2019 |

OTHER PUBLICATIONS

Wermuth, Molecular variations based in isosteric replacements, The Practice of Medicinal Chemistry, 1996, 203-237. (Year: 1996).*
International Search Report and Written Opinion for PCT 2018/083728 mailed Feb. 4, 2019.
Murrough, "Antidepressant Efficacy of Ketamine in Treatment-Resistant Major Depression: A Two Site Randomized Controlled Trial", Am. J. Psychiatry, 2013, vol. 170, p. 1134-1142.
Singh, "Intravenous Eskatamine in Adult Treatment-Resistant Depression: A double-Blind, Double-Randomization, Placebo Controlled Study", Society of Biological Psychiatry, vol. 80, 2016, p. 424-431.
Berman, "Antidepressant effects of Ketamine in depressed patients", Biological Psychiatry, vol. 47, 2000, p. 351-354.

(Continued)

*Primary Examiner* — Sarah Pihonak
*Assistant Examiner* — Padmaja S Rao
(74) *Attorney, Agent, or Firm* — Shelley A. Jones

(57) ABSTRACT

The present invention relates to novel imidazopyrazines of general formula A, processes for their preparation, pharmaceutical compositions containing them and their use in therapy, particularly in the treatment or prevention of conditions having an association with NR2B negative allosteric modulating properties.

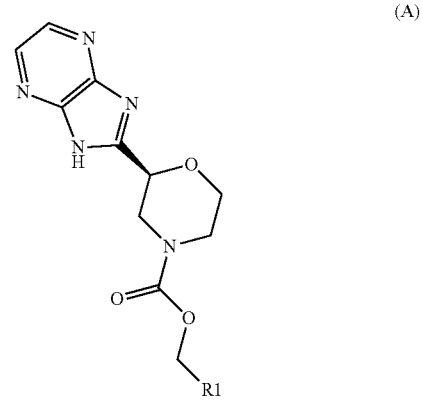

(A)

9 Claims, No Drawings

(56) References Cited

OTHER PUBLICATIONS

Krystal, "Subanesthetic Effects of the Noncompetitive NMDA Antagonist, Ketamine in Humans", Arch. Gen. Psychiatry, 1994, vol. 51, p. 199-214.
Paoletti, NMDA receptor subunit diversity: impact on receptor properties, synaptic plasticity and disease, Nature Reviews, vol. 14, 2013.
Miller, "GluN2B-contaning NMDA receptors regulate depression-like behavior and are critical for the rapid antidepressant actions of ketamine", eLife3e03581, 2014.
Kiselycznyk, "NMDA receptor subunits and associated signaling molecules mediating anti-depressant related effects of NMDA-GluN2B antagonism", Bhav. Nrain Res. 2015, p. 89-95.
Jimemez-Sanchez, "The Role of GluN2A and GluN2B Subunits on the effects of NMDA receptor Antagnonists in modeling Schizophrenia and treating Refractory Depression", Neuropsychopharmacology, 2014.
Taylor, "Absolute Oral Bioavailability of Traxoprodil in Cytochrome P450 2D6 Extensive and Poor Metabolisers", Clin. Pharmacokinet, 2006, vol. 45, p. 989-1001.
Addy, "Single dose Administration of MK-0657, an NR2B-Selective NMDA Antagonist", J. of Clinical Pharmacology, 2009, p. 856-864.
Layton, "Discovery of 3-Substituted Aminocyclopentanes as Potent and Orally Bioavailable NR2B Subtype-Selective NMDA Antagonists", ACS Chem. Neuroscience, 2011.
Traynelis, Glutamate Receptor Ion Channels: Structure, Regualtion and Function, Pharmacology reviews, 2010, vol. 62.
Chaffey, NMDA receptor subtypes, Current Anesthesia and Critical Care, 2008, vol. 19, p. 183-201.
Mony, Allosteric modulators of NR-2B-containing NMDA receptors, Bristish Journal of Pharmacology, vol. 157, 2009.
Preskorn, An Innovative Design to Establish Proof of Concept of the Antidepressant effects of the NR2B Subunit Selective N-Methyl D-Aspartate Antagonist CP-101, 606, Journal of Clinical Pharmacology, vol. 28, 2008.
Beinat, Insights into Structure related activity relationships, Current Medicinal Chem, 2010. vol. 17, p. 4166-4190.
Serafini, The Role of Ketamine in Treatment resistant Depression, Current Neurapharmacology, 2014, vol. 10, p. 444-461.
Sanchez, The role of GluN2A and GluN2B Sununits on the Effects of NMDA Receptor Antagonists in Modeling Schizopgrenia and Treating Refractory Depression, Neuropsychopharmacology, vol. 30, 2014.
Beinat, Insights into Structure-Activity Relationships, Current Medicinal Chem., vol. 17, 2010.
Niu et al., "Synthesis of C8-alkyl-substituted purine analogues by direct alkylation of 8-H purines with tetrahydrofuran catalyzed by CoCl2 6H2O", Chinese chem. letters, 2017, 28, pp. 105-108.
Weed et al., "Negative Allosteric Modulators Selective for the NR2B Subtype of the NMDA Receptor Impair Cognition in Multiple Domains", Neuropsychopharmacology, 2016, 41, pp. 568-577.
Abstract in English for WO2016006593, dated Jan. 14, 2016.

* cited by examiner

IMIDAZOPYRAZINE DERIVATIVES AND THE USE THEREOF AS MEDICAMENT

The present invention relates to novel imidazopyrazines of general formula A

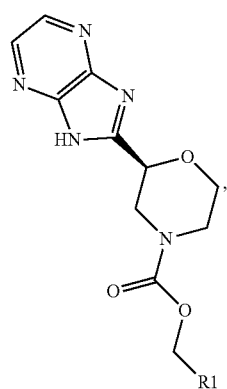

processes for their preparation, pharmaceutical compositions containing them and their use in therapy, particularly in the treatment or prevention of conditions having an association with NR2B negative allosteric modulating properties.

The compounds of the invention according to general formula A show NR2B negative allosteric modulating properties.

Extensive studies over the past twenty years have indicated that N-methyl-D-aspartate receptors (NMDA) play a relevant role in Alzheimer's disease, Parkinson's disease, dyskinesia, stroke, motor neuron disease, psychosis, epilepsy, anxiety, schizophrenia and pain.

The non-selective NMDA receptor antagonist ketamine, (racemic as well as the S enantiomer), a medication mainly used for starting and maintaining anaesthesia, has demonstrated over the last years clinical efficacy in treating major depressive disorder (MDD) at subanaesthetic doses (Murrough et al. 2013, Am J Psychiatry. 170: 1134; Singh et al. 2016, Biol Psychiatry. 80: 424). More precisely, ketamine elicits a rapid onset of efficacy which lasts several days in MDD patients insufficiently responding to standard drug therapy (Berman et al. 2000. Biol Psychiatry 47:351, Serafini et al. 2014. Curr. Neuropharmacol.12:444). However, non-selective NMDA receptor antagonists have a range of undesirable effects which limit their application. In particular dissociative and psychogenic side effects are prominent for the non-selective NMDA receptor antagonists such as ketamine (Krystal et al. 1994. Arch. Gen. Psychiatry 51:199). In the early 1990s, it was found that multiple NMDA receptor subtypes exist, which contain different NR2(A-D) subunits (Paoletti et al., 2013 Nat Rev. Neurosci 14:383). More recently, NR2B subtype selective NMDA receptor negative allosteric modulators (NR2B NAM) have raised interest and have shown potential in a wide range of clinical indications, such as attention, emotion, mood, and pain, as well as being involved in a number of different human disorders (Mony et. al. 2009. Br. J. Pharmacol. 157:1301; Chaffey et al., Current Anaesthesia & Critical Care 19, 183). In particular, NR2B NAM have also demonstrated antidepressant efficacy in the early stage of clinical trials (Preskorn et al. 2008. J Clin Psychopharmacol 70:58). Preclinical studies using NR2B NAM as well as applying various transgenic mice strains have shown that NR2B containing NMDA-receptors are mediating the positive effect of ketamine in e.g. the Forced Swim Test (Miller et al. 2014 eLife 3:e03581; Kiselycznyk et al. 2015, Behav Brain Res, 287:89). Furthermore, selective NR2B NAM have advantages over unselective NMDA receptor antagonists, such as ketamine, due to greatly diminished dissociative and psychotomimetic side effects (Jimenez-Sanchez et al. 2014. Neuropsychopharmacology 39:2673). NR2B NAM described to date have exhibited drawbacks with regard to their receptor pharmacology and/or to other drug properties which have limited potential use in human drug therapy (Taylor, et al., 2006, Clin Pharmacokinet. 45: 989; Addy et al. 2009 J of Clinical Pharmacology 49:856)).

WO2016/29146 discloses compounds of formula (I)

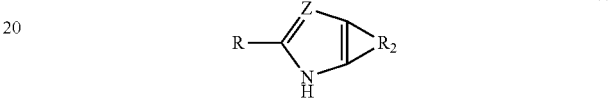

that are inhibitors of methionyl-tRNA synthetase (MetRS) being useful as antibiotics.

Formula (I) in WO2016/29146 encompasses the specific examples 1734, 1744, 1745, 1757 1758, 1785 and 1790 which exhibit a benzimidazole or imidazopyridine substructure.

The compounds of the present invention have surprisingly been found to be potent NR2B negative allosteric modulators (see table 1), whereas the specific examples 1734, 1744, 1745, 1757, 1758, 1785 and 1790 of WO2016/29146 show rather poor negative allosteric modulation of the NR2B ion channel or no activity at all (see table 2).

Further, the compounds of the present invention show good membrane permeability and low to moderate in vitro efflux (see table 3 for MDCK assay MDR1 (p-GP)). Therefore, compounds of the present invention are expected to show a favorable brain penetration which is required for efficacious CNS medicaments.

The MDCK assays provide information on the potential of a compound to pass the blood brain barrier. Permeability measurements across polarized, confluent MDCK-MDR1 cell monolayers grown on permeable filter supports are used as an in vitro absorption model: apparent permeability coefficients (PE) of the compounds across the MDCK-MDR1 cell monolayers are measured (pH 7.4, 37° C.) in apical-to-basal (AB) and basal-to-apical (BA) transport direction. The AB permeability (PEAB) represents drug absorption from the blood into the brain and the BA permeability (PEBA) drug efflux from the brain back into the blood via both, passive permeability as well as active transport mechanisms mediated by efflux and uptake transporters that are expressed on the MDCK-MDR1 cells, predominantly by the overexpressed human MDR1. Identical or similar permeabilities in both transport directions indicate passive permeation, vectorial permeability points to additional active transport mechanisms. Higher PEBA than PEAB (PEBA/PEAB>5) indicates the involvement of active efflux mediated by MDR1, which might compromise the goal to achieve sufficient brain exposure. Therefore, this assay provides valuable support for selection of compounds applicable for further in vivo testing. High permeability not limited by efflux at the blood brain barrier is a favourable characteristic for compounds that are to be used for drugs acting primarily in the CNS. Consequently, to ensure high permeability at the blood brain barrier, it is highly preferred to minimize the efflux (efflux<5) at MDR1 transporter.

Further, the compounds of the present invention are metabolically stable in human liver microsomes (see table 4, metabolic stability). Therefore, compounds of the present invention are expected to have a favorable in vivo clearance and thus the desired duration of action in humans.

Stability in human liver microsomes refers to the susceptibility of compounds to bio-transformation in the context of selecting and/or designing drugs with favorable pharmacokinetic properties. The primary site of metabolism for many drugs is the liver. Human liver microsomes contain the cytochrome P450s (CYPs), and thus represent a model system for studying drug metabolization in vitro. Enhanced stability in human liver microsomes is associated with several advantages, including increased bioavailability and adequate half-life, which can enable lower and less frequent dosing of patients. Thus, enhanced stability in human liver microsomes is a favorable characteristic for compounds that are to be used for drugs.

Consequently, compounds of the present invention must be more viable for human use.

The objective technical problem is thus to provide potent NR2B negative allosteric modulators.

The present invention provides novel imidazopyrazines of formula A

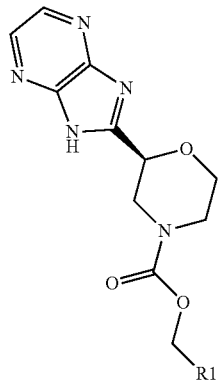

A in which
R$^1$ represents phenyl which is optionally substituted with 1 to 3 substituents selected from the group consisting of fluoro, chloro, methyl, ethyl, cyclopropyl, F$_2$HC—, FH$_2$C—, F$_3$C—;
or a salt thereof, particularly a pharmaceutically acceptable salt thereof.
In another embodiment, in the general formula A
R$^1$ represents phenyl which is optionally substituted with 1 or 2 substituents selected from the group consisting of fluoro, methyl.
In another embodiment, in the general formula A
R$^1$ represents

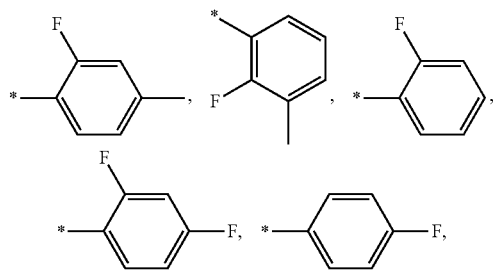

The present invention provides novel imidazopyrazines of general formula A that unexpectedly are potent NR2B negative allosteric modulators.

Another aspect of the invention refers to compounds according to formula A as NR2B negative allosteric modulators having appropriate membrane permeability and low to moderate in vitro efflux.

Another aspect of the invention refers to compounds according to formula A as NR2B negative allosteric modulators having high metabolic stability in human liver microsomes.

Another aspect of the invention refers to compounds according to formula A as NR2B negative allosteric modulators having appropriate membrane permeability, low to moderate in vitro efflux and high metabolic stability in human liver microsomes.

Another aspect of the invention refers to pharmaceutical compositions, containing at least one compound according to formula A optionally together with one or more inert carriers and/or diluents.

A further aspect of the present invention refers to compounds according to formula A, for the use in the prevention and/or treatment of disorders associated with NR2B negative allosteric modulators.

Another aspect of the invention refers to processes of manufacture of the compounds of the present invention.

Preparation

The following schemes shall illustrate generally how to manufacture the compounds according to general formula A and the corresponding intermediate compounds by way of example. The abbreviated substituents may be as defined above if not defined otherwise within the context of the schemes.

Scheme 1: Method A

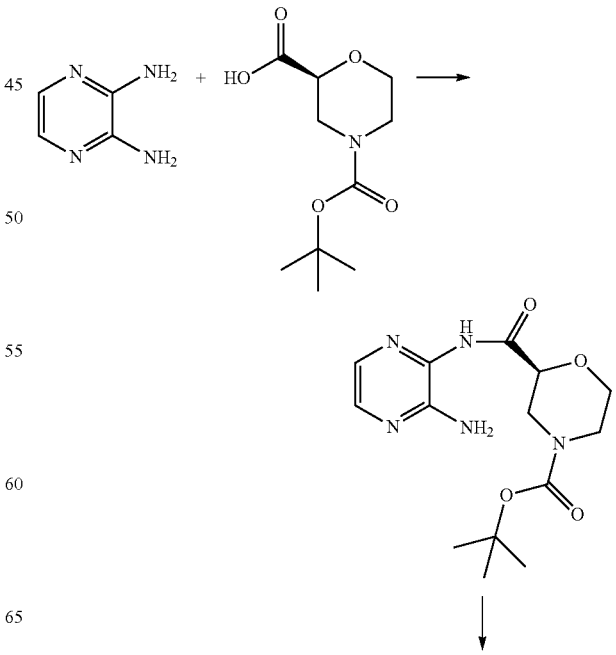

5
-continued
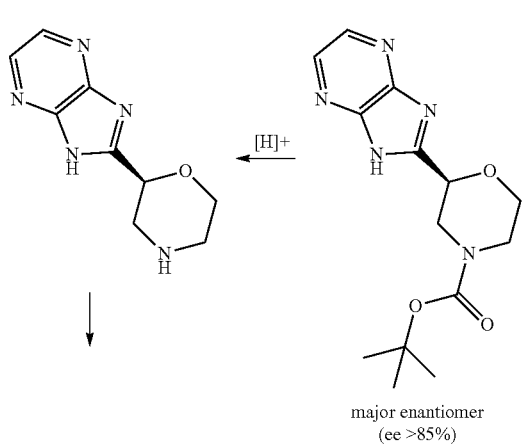
major enantiomer
(ee >85%)
6
-continued
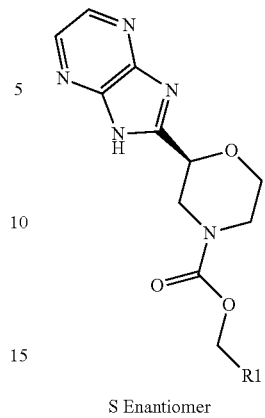
S Enantiomer
Scheme 2: Method B
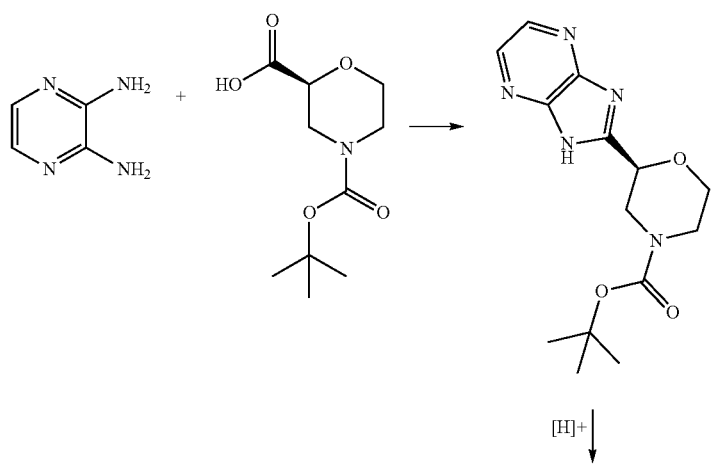
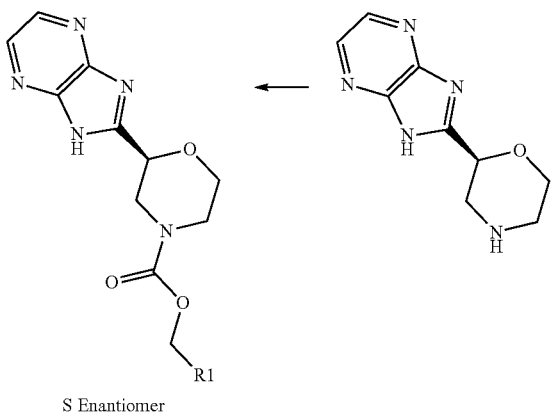
S Enantiomer Alternatively, the synthesis can be performed using racemic morpholine-2,4-dicarboxylic acid 4-tert-butyl ester as starting material.

Scheme 1 and 2 can be successfully used for gram scale synthesis of the final compounds starting from 40 mmoles of the desired substituted morpholine (racemic or the S enantiomer), using an excess of the desired substituted benzyl alcohol, DIPEA (3 equivalents), the needed coupling agent such as CDI and DMF as solvent.

An alternative gram scale synthesis can be performed using the corresponding morpholine (racemic or the S enantiomer; 40 mmol), TEA (2.5 equivalents), a slight excess of the required imidoylcarbonate and a 1/1 (volume/volume) mixture $CH_3CN/THF$ as solvent. The final compounds can be obtained with good to high enantiomeric excess; alternatively, chiral separation can be applied to obtain the pure enenantiomers.

In schemes 1 and 2, the substituent $R^1$ has the meaning as defined for general formula A, all embodiments of the invention that directly refer thereto and specifically the meaning as defined in the claims.

GENERAL DEFINITIONS

Terms not specifically defined herein should be given the meanings that would be given to them by one skilled in the art in light of the disclosure and the context.

In case a compound of the present invention is depicted in form of a chemical name as well as a formula, the formula shall prevail in case of any discrepancy.

An asterisk may be used in sub-formulas to indicate the bond which is connected to the core molecule or to the substituent to which it is bound as defined.

The term "substituted" as used herein means that any one or more hydrogens on the designated atom is replaced with a selection from the indicated group, provided that the designated atom's viable valence number is not exceeded, and that the substitution results in a stable compound.
Stereochemistry:

Unless specifically indicated, throughout the specification and the appended claims, a given chemical formula or name shall encompass rotamers, tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.
Salts:

The phrase "pharmaceutically acceptable" is employed herein to refer to those compounds, materials, compositions, and/or dosage forms which are, within the scope of sound medical judgment, suitable for use without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt or a complex with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydro-bromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-amino-methane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoro-acetate salts) also comprise a part of the invention.

BIOLOGICAL ASSAYS AND DATA

List of Abbreviations

DMEM Dulbecco's Modified Eagle's Medium
FBS fetal Bovine Serum
FLIPR fluorometric imaging plate reader
HEK293 cell line derived from human embryonic kidney cells
HEPES hydroxyethyl-piperazineethane-sulfonic acid buffer
MDCK Madin-Darby canine kidney
MDR1 Multi drug resistance protein 1
p-GP p-Glycoprotein
In-Vitro Effect:
Determination of In Vitro Pharmacological Activity The activity of the compounds of the invention may be demonstrated using the following in vitro NMDA NR1/NR2b cell assays:
Method:

A human HEK293 cell line with tetracyclin-inducible expression of NMDA NR1/NR2B receptor was used as a test system for compound efficacy and potency. The cell line was purchased from ChanTest, Catalog #CT6121. Compound activity was determined by measuring the effect of compounds on intracellular calcium concentration induced by glycine/glutamate agonism in a FLIPRtetra system (Molecular Devices).
Cell Culture:

The cells were obtained as frozen cells in cryo-vials and stored until use at −150° C. Cells were grown in culture medium (DMEM/F12, 10% FBS, 5 µg/mL Blasticidin, 150 µg/mL Zeozin, 500 µg/mL Geneticin). It is important that density does not exceed 80% confluence. For sub-culturing the cells were detached from flasks by Versene. For the assay, cells were detached, washed twice with induction medium ($DMEM/F_{12}$ without glutamine, 10% FBS, 2 µg/mL Tetracycline, 2 mM Ketamine) and seeded to 384 well pure coat amine plates (BD 359324, 50000 cells per well in 50 µl) 48 h prior to assay in induction medium.
Compound Preparation The test compounds were dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions were prepared in duplicate, further intermediate dilutions (1:37.5) of the substances were carried out with aqueous assay buffer (137 mM NaCl, 4 mM KCl, 1.8 mM CaCl, 10 mM HEPES, 10 mM Glucose, pH 7,4) resulting in a compound concentration 3 times above the final test concentration and DMSO at 2.7% resulting in 0.9% final DMSO concentration in the assay.

FLIPR Assay:

At the assay day cells were washed 3× with assay buffer, 10 µL buffer remained in the wells after washing. 10 µL Ca kit loading buffer (AAT Bioquest) was added to the cells and the plates were incubated with lid for 60 minutes at r.t. 20 µl assay buffer containing 60 µM glycine (20 µM final) and 3 µM glutamate (1 µM final) was added to column 1-23. Fluorescence (indicating the calcium influx as a result of the NR1/NR2B ion channel activation) was read on the FLIPRtetra device for 60 seconds to monitor the glutamate induced effects. After 2 minutes 20 µL of compound or controls (row 1-22) in assay buffer were carefully added to the wells. Fluorescence was read on the FLIPR tetra device for additional 6 minutes to monitor the compound induced effects after activation by agonists. The average of 2 measurements at 5 minutes and 5 min 10 seconds after compound addition is calculated and further used for IC50 calculations. Each assay microtiter plate contained wells (in column 23 or 24) with DMSO controls instead of compound as controls for glycine/glutamate induced fluorescence (high controls) and wells with 1 µM of a reference NR2b NAM as low controls (Compound 22; reference: Layton, Mark E et al, ACS Chemical Neuroscience 2011, 2(7), 352-362).

Data Evaluation and Calculation:

The output file of the reader contains the well number and measured average fluorescence units. For data evaluation and calculation, the measurement of the low control was set as 0% control and the measurement of the high control was set as 100% control. The IC50 values were calculated using the standard 4 parameter logistic regression formula. Calculation: [y=(a−d)/(1+(x/c)^B)+d], a=low value, d=high value; x=conc M; c=IC50 M; b=slope.

NR2B negative allosteric modulators covered by general structure A and exhibiting a low $IC_{50}$ value are preferred.

TABLE 1

In vitro affinity of the compounds of the present invention as obtained in the FLIPR assay

| Example number | IC50 [nM] |
| --- | --- |
| 1 | 90 |
| 3 | 725 |
| 4 | 382 |
| 5 | 477 |
| 10 | 735 |
| 12 | 210 |

TABLE 2

In vitro affinity of the closest prior art compounds (examples 1734, 1744, 1745, 1757, 1758, 1785 and 1790 in WO2016/29146) as obtained in the same FLIPR assay as compounds in table 1

| Example number in WO2016/29146 | IC50 [nM] |
| --- | --- |
| 1734 | >8885 |
| 1744 | >8889 |
| 1745 | >8898 |
| 1757 | >8900 |

TABLE 2-continued

In vitro affinity of the closest prior art compounds (examples 1734, 1744, 1745, 1757, 1758, 1785 and 1790 in WO2016/29146) as obtained in the same FLIPR assay as compounds in table 1

| Example number in WO2016/29146 | IC50 [nM] |
| --- | --- |
| 1758 | >8884 |
| 1785 | 6200 |
| 1790 | >8887 |

MDCK Assay MDR-1 (p-GP)

Apparent permeability coefficients (Papp) of the compounds across the MDCK-MDR1 monolayers (MDCKII cells transfected with human MDR1 cDNA expression plasmid) are measured in apical-to-basal (AB) and basal-to-apical (BA) direction.

MDCK-MDR1 cells ($6×10^5$ cells/$cm^2$) are seeded on filter inserts (Corning, Transwell, polycarbonate, 0.4 µm pore size) and cultured for 9 to 10 days. Compounds dissolved in DMSO stock solution (1-20 mM) are diluted with HTP-4 aqueous buffer (128.13 mM NaCl, 5.36 mM KCl, 1 mM MgSO4, 1.8 mM $CaCl_2$), 4.17 mM $NaHCO_3$, 1.19 mM Na2HPO4, 0.41 mM NaH2PO4, 15 mM HEPES, 20 mM glucose, pH 7.4) supplemented with 0.25% BSA to prepare the transport solutions (final concentration: 1 or 10 µM, final DMSO <=0.5%). The transport solution is applied to the apical or basolateral donor side for measuring A-B or B-A permeability, respectively. The receiver side contains HTP-4 buffer supplemented with 0.25% BSA. Samples are collected at the start and end of experiment from the donor and at various time intervals for up to 2 hours also from the receiver side for concentration measurement by HPLC-MS/MS.

Sampled receiver volumes are replaced with fresh receiver solution. Efflux ratio is calculated dividing the Papp (b-a) values by the Papp (a-b) values. Results are shown in table 3.

TABLE 3

| Ex. | Papp (a-b) mean [10−6 cm/s] | efflux ratio |
| --- | --- | --- |
| 1 | 33 | 1.6 |
| 3 | 61 | 0.7 |
| 4 | 57 | 0.8 |
| 5 | 40 | 1.4 |
| 10 | 23 | 2.9 |
| 12 | 31 | 1.8 |

The experimental results above show that compounds of the present invention are potent NR2B NAMs having good membrane permeability and low to moderate in vitro efflux.

Metabolic Stability

The metabolic degradation of the test compound was assayed at 37° C. with pooled human liver microsomes. The final incubation volume of 60 l per time point contains TRIS buffer pH 7.6 at room temperature (0.1 M), magnesium chloride (5 mM aqueous solution), microsomal protein (1 mg/mL for human) and the test compound at a final concentration of 1 µM. Following a short preincubation period at 37° C., the reactions were initiated by addition of betanicotinamide adenine dinucleotide phosphate, reduced form (NADPH, 1 mM), and terminated by transferring an aliquot into solvent after different time points. After centrifugation (10000 g, 5 min), an aliquot of the supernatant was assayed by LC-MS/MS for the amount of parent compound. The half-life was determined by the slope of the semi-logarithmic plot of the concentration-time profile. Results are shown in Table 4.

TABLE 4

| Ex. | Half-life - t½ [min] human liver microsomes |
|---|---|
| 1 | 31.5 |
| 3 | 8 |
| 4 | >130 |
| 5 | >130 |
| 10 | >130 |
| 12 | 36 |

The present invention provides compounds according to formula A that unexpectedly result in a favorable combination of the following key parameters:
1) NR2B negative allosteric modulation,
2) favorable stability in human liver microsomes, and
3) moderate to low in vitro efflux at MDR1 transporter.

Pharmaceutical Composition

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Use in Treatment/Method of Use

Human therapeutic applications of NR2B NAM have been summarized in reviews by Traynelis et al. (Traynelis et al., Pharmacology Reviews, 2010, 62:405), Beinat et al. (Beinat et al., Current Medicinal Chemistry, 2010, 17:4166) and Mony et al. (Mony et al., British J. Pharmacology, 2009, 157:1301).

The present invention relates to compounds which are useful in the treatment of psychiatric disorders, diseases and conditions wherein negative allosteric modulation of NR2B is of therapeutic benefit, including: (1) mood disorders and mood affective disorders; (2) schizophrenia spectrum disorders; (3) neurotic, stress-related and somatoform disorders including anxiety disorders; (4) disorders of psychological development; (5) behavioral syndromes associated with physiological disturbances and physical factors; (6) substance-related and addictive disorders; (7) disease associated with symptoms of negative and positive valence.

In view of their pharmacological effect, compounds of the present invention are suitable for use in the treatment of a disorder, disease or condition selected from the list consisting of
  (1) treatment of mood disorders and mood affective disorders including bipolar disorder I depressed, hypomanic, manic and mixed form; bipolar disorder II; depressive disorders, such as single depressive episode or recurrent major depressive disorder, minor depressive disorder, depressive disorder with postpartum onset, depressive disorders with psychotic symptoms; major depressive disorder with or without concomitant anxious distress, mixed features, melancholic features, atypical features, mood-congruent psychotic features, mood-incongruent psychotic features, catatonia.
  (2) treatment of mood disorders belonging to the schizophrenia spectrum and other psychotic disorders including schizophrenia and schizoaffective disorder with associated negative and cognitive symptoms.
  (3) treatment of disorders belonging to the neurotic, stress-related and somatoform disorders including anxiety disorders, general anxiety disorder, panic disorder with or without agoraphobia, specific phobia, social phobia, chronic anxiety disorders; obsessive compulsive disorder; reaction to sever stress and adjustment disorders, such as post-traumatic stress disorder; other neurotic disorders such as depersonalisation-derealisation syndrome.
  (4) treatment of disorders of psychological development including pervasive developmental disorders, including Asperger's syndrome and Rett's syndrome, autistic disorders, childhood autism and overactive disorder associated with mental retardation and stereotyped movements, specific developmental disorder of motor function, specific developmental disorders of scholastic skills, attention deficit/hyperactivity disorder.
  (5) treatment of behavioral syndromes associated with physiological disturbances and physical factors including mental and behavioural disorders associated with the puerperium, including postnatal and postpartum depression; eating disorders, including anorexia nervosa and bulimia nervosa and other impulse control disorders.
  (6) treatment of disorders of substance-related and addictive disorders, which are substance use disorders induced by alcohol, cannabis, hallucinogen, stimulant, hypnotic, tobacco.
  (7) treatment of disease associated with symptoms of negative and positive valence including anhedonia, sustained threat and loss, suicidal ideation.

As used herein, unless otherwise noted, the terms "treating", "treatment" shall include the management and care of a human subject or human patient for the purpose of com-bating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

According to another aspect, the present invention provides a compound of formula A or a pharmaceutically acceptable salt thereof for use in the treatment and/or prevention of the above mentioned conditions.

According to another aspect, the present invention provides a compound of formula A according to any one of the preceding aspects characterized in that the compound of formula A is used in addition to behavioural therapy, TMS (transcranial magnetic stimulation), ECT (electroconvulsive therapy) and other therapies.

Combination Therapy

Compounds according to the present invention can be combined with other treatment options known to be used in the art in connection with a treatment of any of the indications the treatment of which is in the focus of the present invention.

According to another aspect, the present invention provides a compound of formula A according to any one of the preceding aspects characterized in that the compound of formula A is administered in addition to treatment with one or more antidepressant selected from the list consisting of duloxetine, escitalopram, bupropion, venlafaxine, desvenlafaxine, sertraline, paroxetine, fluoxetine, vortioxetine, mirtazapine, citalopram, vilazodone, trazodone, amitriptyline, clomipramine, agomelatine, levomilnacipran, lithium, doxepin, nortriptyline. The term "antidepressant" shall mean any pharmaceutical agent or drug which can be used to treat depression or diseases assocaited with depressive symptoms.

According to another aspect, the present invention provides a compound of formula A according to any one of the preceding aspects characterized in that the compound of formula A is administered in addition to treatment with one or more antipsychotic selected from the list consisting of aripiprazole, paliperidone palmitate, lurasidone, quetiapine, risperidone, olanzapine, paliperidone, brexpiprazole, clozapine, asenapine, chlorpromazine, haloperidol, cariprazine, ziprasidone, amisulpride, iloperidone, fluphenazine, blonanserin, aripiprazole lauroxil. The term "antipsychotic" shall mean any pharmaceutical agent or drug which can be used to treat diseases associated with psychotic or depressive symptoms.

According to another aspect, the present invention provides a compound of formula A according to any one of the preceding aspects characterized in that the compound of formula A is administered in addition to treatment with one or more psychostimulant selected from the list consisting of lisdexamfetamine, methylphenidate, amfetamine, dexamfetamine, dexmethylphenidate, armodafinil, modafinil. The term "psychostimulant" shall mean any pharmaceutical agent or drug which can be used to treat diseases like mood disorders, or impulse control disorders.

According to another aspect, the present invention provides a compound of formula A according to any one of the preceding aspects characterized in that the compound of formula A is administered in addition to treatment with nootropics selected from the list consisting of oxiracetam, piracetam, or the natural product St John's-wort.

According to another aspect, the present invention provides a compound of formula A which is administered in addition to treatment with one or more antidepressant, antipsychotic, psychostimulant, nootropics or natural product according to any one of the preceding aspects characterized in that the combination of compound of formula A and one or more antidepressant, antipsychotic, psychostimulant, nootropics or natural product is used in addition to behavioural therapy, TMS (transcranial magnetic stimulation), ECT (electroconvulsive therapy) and other therapies.

EXPERIMENTAL SECTION

Abbreviations

ACN acetonitrile
APCI Atmospheric pressure chemical ionization
Boc tert-butyloxycarbonyl
CDI 1,1'-carbonyldiimidazole
C02 Carbon Dioxide
d day
DA Diode Array
DAD Diode Array Detector
DCM dichloromethane
DIPE diisopropylether
DIPEA diisopropylethylamine
DMF dimethylformamide
ee, e.e. enantiomeric excess
ELSD Evaporative Light Scattering Detector
ESI electrospray ionization (in MS)
EtOAc ethylacetate
EtOH ethanol
Exp. example
h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
IPA Isopropanol
M molar (mol/L)
MeOH methanol
min minute(s)
MS mass spectrometry
MW molecular weight
$NH_3$ ammonia
PSI Pound per square inch
rt room temperature
$R_t$ retention time
scCO2 supercritical CO2
Sol Solvent
solv solvent
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
SFC Supercritical fluid chromatography General Analytics All reactions were carried out using commercial grade reagents and solvents. NMR spectra were recorded on a Bruker AVANCE IIIHD 400 MHz instrument using TopSpin 3.2 p16 software. Chemical shifts are given in parts per million (ppm) downfield from internal reference trimethylsilane in δ units. Selected data are reported in the following manner: chemical shift, multiplicity, coupling constants (J), integration. Analytical thin-layer chromatography (TLC) was carried out using Merck silica gel 60 F254 plates. All compounds were visualized as single spots using short wave UV light. Low resolution mass spectra were obtained using a liquid chromatography mass spectrometer (LCMS) that consisted of an Agilent 1100 series LC coupled to a Agilent 6130 quadru-pole mass spectrometer (electrospray positive ionization).

Methods:

For solvent mixtures used for HPLC-MS methods and Chiral SFC analytical methods, % solvent are given as volume percent of the corresponding solvent.

HPLC-MS methods:

| Method 1 | |
|---|---|
| Method Name: | Z011_S03 |
| Device description: | Agilent 1200 with DA- and MS-Detector |
| Column: | XBridge C18_3.0 × 30 mm_2.5 µm |
| Column producer: | Waters |
| Description: | |

| Method Name: Z011_S03 | | | | | |
|---|---|---|---|---|---|
| Gradient/ Solvent Time [min] | % Sol [Water 0.1% NH₃] | % Sol [Acetonitrile] | Flow [ml/min] | Temp [° C.] | Back pressure [PSI] |
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Chiral SFC analytical methods:

| Method 2: I_C2_20_MeOH_NH₃_001 | |
|---|---|
| Method Name: | I_C2_20_MEOH_NH₃_001 |
| Device description: | Agilent 1260 SFC with DAD and ELSD |
| Column: | Lux ® Cellulose-2_4.6 × 250 mm_5 µm |
| Column producer: | Phenomenex |

| Gradient/ Solvent Time [min] | % Sol [scCO2] | % Sol [MeOH 20 mM NH₃] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

| Method 3: I_C2_40_IPA_NH₃_001 | |
|---|---|
| Method Name: | I_C2_40_IPA_NH₃_001 |
| Device description: | Agilent 1260 SFC with DAD and ELSD |
| Column: | Lux ® Cellulose-2_4.6 × 250 mm_5 µm |
| Column producer: | Phenomenex |

| Gradient/ Solvent Time [min] | % Sol [scCO2] | % Sol [IPA 20 mM NH₃] | Flow [ml/min] | Temp [° C.] | Back pressure [PSI] |
|---|---|---|---|---|---|
| 0.0 | 60.0 | 40.0 | 4.0 | 40.0 | 2175.0 |
| 10.0 | 60.0 | 40.0 | 4.0 | 40.0 | 2175.0 |

| Method 4: I_SA_20_MEOH_NH₃_001 | |
|---|---|
| Method Name: | I_SA_20_MEOH_NH₃_001 |
| Device description: | Agilent 1260 SFC with DAD and MS |
| Column: | CHIRAL ART ® Amylose SA_4.6 × 250 mm_5 µm |
| Column producer: | YMC |

| Gradient/ Solvent Time [min] | % Sol [scCO2] | % Sol [MeOH 20 mM NH₃] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Preparation of Intermediates:

Example 1a

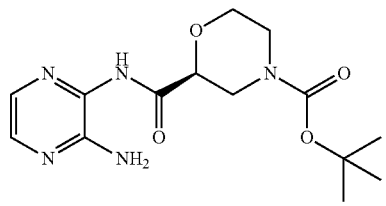 [SMILES: CC(C)(C)OC(=O)N1CCO[C@H](C(=O)Nc2nccnc2N)C1]

S-Morpholin-2,4-dicarboxylic acid 4-tertbutylester (1.26 g, 5.45 mmol) was dissolved in DMF (20 ml). Then HATU (2.28 g, 5.99 mmol) was added, followed by Pyrazine-2,3-diamine (600 mg, 5.45 mmol, CAS No. 13134-31-1) and TEA (1.52 ml, 10.9 mmol). The reaction mixture was stirred 20 h at room temmperature before the work-up: The reaction mixture was filtered with a glass filter and the filtrate was concentrated in vacuo. The residue was treated with 40 mL H₂O and stirred for 2 h. The obtained precipitate was filtered off and dried in the air. Obtained 1.60 g of the desired product.

HPLC-MS; Method: Z011_S03; $R_t$ [min]: 0.76    MS: 324 (M + H)⁺

Example 2a—Method A (According to Scheme 1)

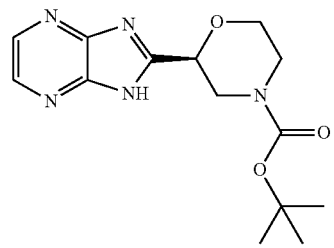 [SMILES: CC(C)(C)OC(=O)N1CCO[C@H](c2nc3nccnc3[nH]2)C1]

A mixture of example 1a (1.60 g, 4.95 mmol), potassium carbonate (2.74 g, 19.8 mmol) and isopropanol (50 ml) was stirred for 6 h at 80° C. The precipitate was filtered off, washed with isopropanol and the filtrate was concentrated in vacuo. The residue was dried overnight. Obtained 1.50 g of the desired product.

HPLC-MS; Method: Z011_S03; $R_t$ [min]: 0.58    MS: 306 (M + H)⁺

Example 2a—Method B (Direct Cyclisation, According to Scheme 2)

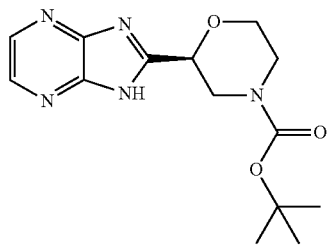 [SMILES: CC(C)(C)OC(=O)N1CCO[C@H](c2nc3nccnc3[nH]2)C1]

S-Morphline-2,4-dicarboxylic acid 4-tertbutylester (3.15 g, 13.62 mmol) was dissolved in DMF (30 ml). Then HATU (5.7 g, 15 mmol) was added, followed by Pyrazine-2,3-diamine (1.5 g, 13.62 mmol, CAS No. 13134-31-1) and TEA (3.8 ml, 27.2 mmol). The reaction mixture was stirred 7 h at room temperature before the work-up: The reaction mixture was filtered with a glass filter and the filtrate was concentrated in vacuo. The residue was treated with 100 mL H$_2$O and stirred for 12 h. The obtained precipitate was filtered off and dried in the air. Obtained 2.0 g of the desired cyclised product.

HPLC-MS; Method: Z011_S03; R$_t$ [min]: 0.76  MS: 306 (M + H)$^+$
Chiral SFC; Method: I_C2_20_MEOH_NH3_001;  ee: 100%
R$_t$ [min]: 3.36 min The residue was triturated with 3 mL DIPE, filtered and dried in the air. Obtained 157 mg of the desired compound.

Example 3a

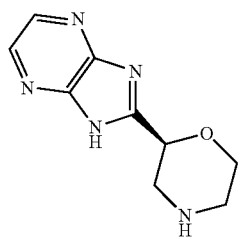 [SMILES: c1cnc2[nH]c([C@@H]3CNCCO3)nc2n1]

Example 2a (2 g, 6.55 mmol) was dissolved in DCM (120 ml), HCl in dioxane (4 M, 9.83 ml, 39.3 mmol) was added and the reaction mixture was stirred 3.5 h at rt. The solvents were evaporated in vacuo and the obtained residue was used as such in the next step. Obtained 1.8 g of the desired product as a salt.

Chiral SFC; Method: I_C2_20_MEOH_NH3_001;  MS: 206 (M + H)$^+$
R$_t$ [min]: 6.48 min  ee: 100%

EXEMPLARY EMBODIMENTS

Example 1

(2-Fluoro-4-methylphenyl)methanol (151 mg; 1.08 mmol, CAS No. 252004-38-9) and CDI (175 mg; 1.08 mmol) were mixed together in DMF (3 ml); the reaction mixture was heated at 50° C. during 30 minutes. Example 3a (150 mg; 0.54 mmol) and DIPEA (0.28 ml; 1.62 mmol) were then added in sequence and the reaction mixture was stirred 2 hours at rt. The reaction mixture was diluted with 3 ml of a mixture MeOH/Water (1/1; volume/volume) before being filtered and separated via semipreparative HPLC.

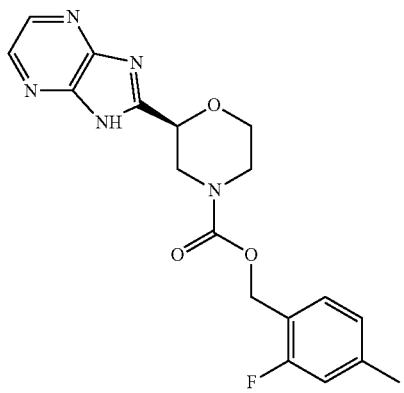 [SMILES: Cc1ccc(COC(=O)N2CCO[C@H](c3nc4nccnc4[nH]3)C2)c(F)c1]

Example 1

HPLC-MS; Method: Z011_S03; R$_t$ [min]: 0.68  MS: 372 (M + H)$^+$
Chiral SFC; Method: I_SA_20_MEOH_NH$_3$_001  Rt [min]: 4.13
  ee: 92.4%

Example 3

(2-Fluoro-3-methylphenyl)methanol (151 mg; 1.08 mmol, CAS No. 307975-03-7) and CDI (175 mg; 1.08 mmol) were mixed together in DMF (3 ml); the reaction mixture was heated at 50° C. during 30 minutes. Example 3a (150 mg; 0.54 mmol) and DIPEA (0.28 ml; 1.62 mmol) were then added in sequence and the reaction mixture was stirred 16 hours at rt. The reaction mixture was diluted with 3 ml of a mixture MeOH/Water (1/1; volume/volume) before being filtered and separated via semipreparative HPLC. Obtained 80 mg of the desired compound.

Example 3

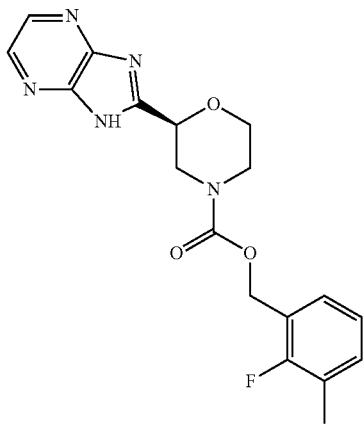 [SMILES: Cc1cccc(COC(=O)N2CCO[C@H](c3nc4nccnc4[nH]3)C2)c1F]

| HPLC-MS; Method: Z011_S03; $R_t$ [min]: 0.69 | MS: 372 (M + H)$^+$ |
| --- | --- |
| Chiral SFC; Method: I_SA_20_MEOH_NH$_3$_001 | Rt [min]: 3.3 |
| | ee: 94.4% |

Example 4

(2-Fluorophenyl)methanol (116 µl; 1.08 mmol, CAS No. 446-51-5) and CDI (175 mg; 1.08 mmol) were mixed together in DMF (3 ml); the reaction mixture was heated at 50° C. during 30 minutes. Example 3a (150 mg; 0.54 mmol) and DIPEA (0.28 ml; 1.62 mmol) were then added in sequence and the reaction mixture was stirred 3 hours at rt.

The reaction mixture was diluted with 3 ml of a mixture MeOH/Water (1/1; vol-ume/volume) before being filtered and separated via semipreparative HPLC. Obtained 98 mg of the desired compound.

Example 4

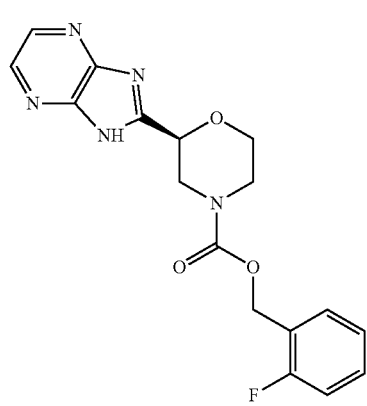 [SMILES: O=C(OCc1ccccc1F)N1CCO[C@H](c2nc3nccnc3[nH]2)C1]

| HPLC-MS; Method: Z011_S03; $R_t$ [min]: 0.63 | MS: 358 (M + H)$^+$ |
| --- | --- |
| Chiral SFC; Method: I_SA_20_MEOH_NH$_3$_001 | Rt [min]: 3.37 |
| | ee: 100% |

Example 5

Example 5 was synthesised in analogy to Example 4. Starting materials: Example 3a (150 mg, 0.54 mmol) and (2,4-Difluorophenyl)methanol (121 µl, 1.08 mmol, CAS No. 56456-47-4). The crude was purified via semipreparative HPLC. Obtained 112 mg of the desired compound.

Example 5

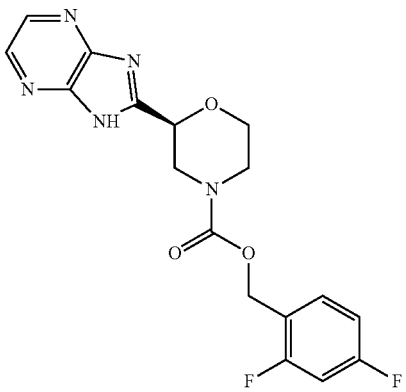 [SMILES: O=C(OCc1ccc(F)cc1F)N1CCO[C@H](c2nc3nccnc3[nH]2)C1]

| HPLC-MS; Method: Z011_S03; $R_t$ [min]: 0.64 | MS: 376 (M + H)$^+$ |
| --- | --- |
| Chiral SFC; Method: I_SA_20_MEOH_NH$_3$_001 | Rt [min]: 3.18 |
| | ee: 100% |

Example 10

(4-Fluorophenyl)methanol (157 µl, 1.44 mmol, CAS No. 459-56-3) was dissolved in DMF (6 ml); TEA (0.3 ml; 2.16 mmol) was added followed by Bis-[1,2,4]triazol-1-yl-methanone (236 mg, 1.44 mmol) and Example 3a (200 mg, 0.72 mmol). The reaction mixture was stirred 2 h at 50° C. before being diluted with H$_2$O/MeOH (4 ml; 1/1; volume/volume mixture), filtered and purified with semipreparative HPLC.

Obtained 150 mg of the desired compound.

Example 10

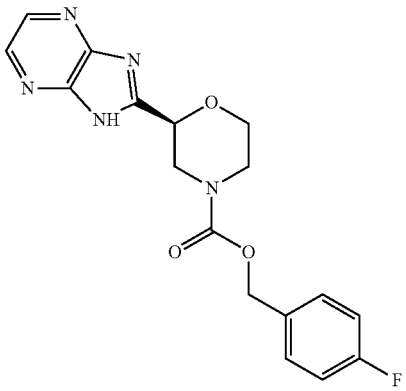 [SMILES: O=C(OCc1ccc(F)cc1)N1CCO[C@H](c2nc3nccnc3[nH]2)C1]

| HPLC-MS; Method: Z011_S03; $R_t$ [min]: 0.61 | MS: 358 (M + H)$^+$ |
| --- | --- |
| Chiral SFC; Method : I_SA_20_MEOH_NH$_3$_001 | Rt [min]: 4.25 |
| | ee: 100% |

Example 12

Example 12 was synthesised in analogy to Example 10. Starting materials: Example 3a (200 mg, 0.72 mmol) and (4-Methylphenyl)methanol (176 mg, 1.44 mmol, CAS No. 589-18-4). The reaction mixture was purified via semi-preparative HPLC. Obtained 117 mg of the desired compound.

Example 12

HPLC-MS; Method: Z011_S03; R$_t$ [min]: 0.67  MS: 354 (M + H)$^+$
Chiral SFC; Method: I_C2_40_IPA_NH$_3$_001  Rt [min]: 3.65
ee: 66.7%

The invention claimed is:

1. A compound of formula A

A in which

R$^1$ represents phenyl which is optionally substituted with 1 to 3 substituents selected from the group consisting of fluoro, chloro, methyl, ethyl, cyclopropyl, F$_2$HC—, FH$_2$C—, and F$_3$C—;

or a pharmaceutically acceptable salt thereof.

2. The compound according to claim 1, or pharmaceutically acceptable salt thereof, wherein R$^1$ represents phenyl which is optionally substituted with 1 or 2 substituents selected from the group consisting of fluoro and methyl.

3. The compound according to claim 1, or pharmaceutically acceptable salt thereof, wherein R$^1$ represents 4. An (S)-enantiomer of a compound according to claim 1, selected from the group consisting of:

| Exp | |
|---|---|
| 1 | |
| 5 | |

| Exp | |
|---|---|
| 3 | 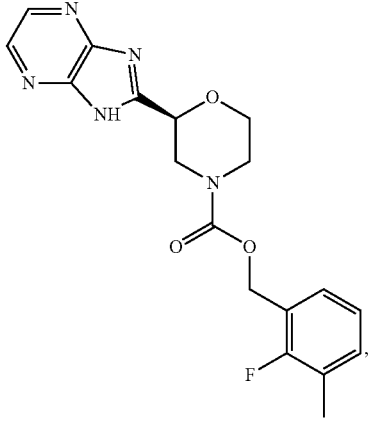 [SMILES: Cc1cccc(COC(=O)N2CCO[C@H](c3nc4nccnc4[nH]3)C2)c1F] |
| 10 | |
| 4 | , and |

| Exp | |
|---|---|
| 12 | 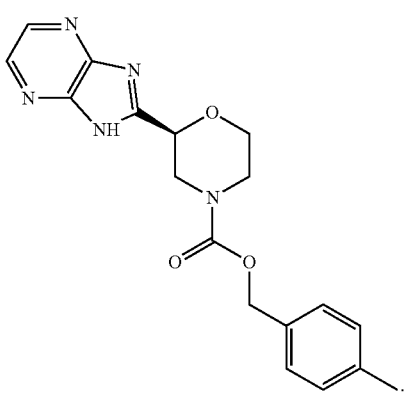 [SMILES: Cc1ccc(COC(=O)N2CCO[C@H](c3nc4nccnc4[nH]3)C2)cc1] |

5. A pharmaceutically acceptable salt of a compound according to claim 1.

6. A pharmaceutical composition comprising the compound according to claim 1 in admixture with a pharmaceutically acceptable adjuvant, diluent and/or carrier.

7. A method for treating and/or preventing a psychiatric disease and/or disorder, comprising administering to a patient in need thereof the compound according to claim 1, or a pharmaceutically acceptable salt thereof, wherein the disease and/or disorder is:

bipolar disorder I depressed, hypomanic, manic or mixed form;

bipolar disorder II;

single depressive episode, recurrent major depressive disorder, minor depressive disorder, depressive disorder with postpartum onset, depressive disorders with psychotic symptoms; or major depressive disorder with or without concomitant anxious distress, mixed features, melancholic features, atypical features, mood-congruent psychotic features, mood-incongruent psychotic features, or catatonia.

8. The method according to claim 7, characterized in that the compound is administered in combination with another antidepressant drug.

9. The method according to claim 7, wherein the patient is further undergoing behavioural therapy.

* * * * *